Figure 1:
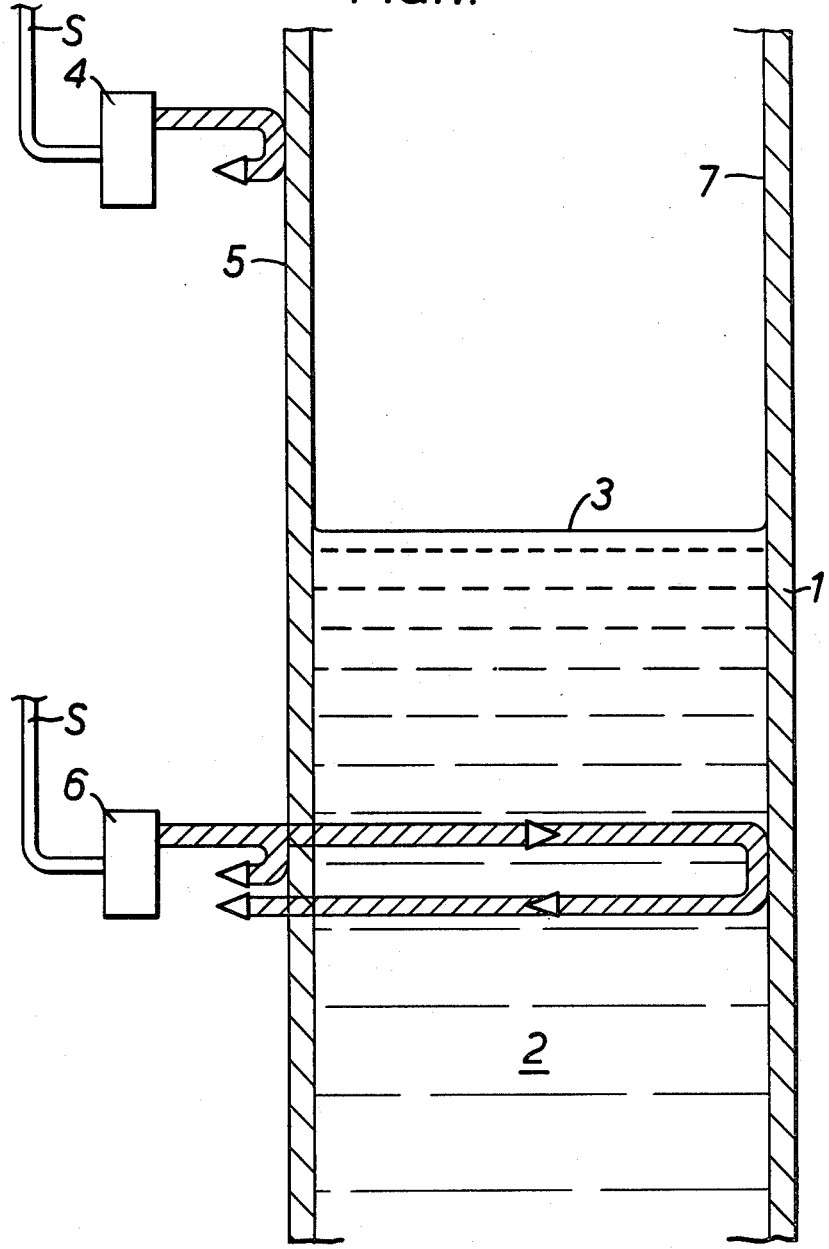

United States Patent [19]

Bennett et al.

[11] 4,445,363

[45] May 1, 1984

[54] DEVICE FOR DETECTING FLOODING OF A HOLLOW STRUCTURE

[75] Inventors: Alan Bennett, Fenham; Derek Brown, Whitley Bay, both of England

[73] Assignee: British Gas Corporation, London, England

[21] Appl. No.: 349,984

[22] Filed: Feb. 18, 1982

[30] Foreign Application Priority Data

Mar. 6, 1981 [GB] United Kingdom ............... 8107122

[51] Int. Cl.³ .............................................. G01M 3/24
[52] U.S. Cl. .................................................. 73/40.5 A
[58] Field of Search ................ 73/40.5 A, 40.5 R, 40, 73/290 V

[56] References Cited

U.S. PATENT DOCUMENTS 4,242,744 12/1980 Rottmar ........................... 73/40.5 A

*Primary Examiner*—Gerald Goldberg
*Assistant Examiner*—Joseph W. Roskos
*Attorney, Agent, or Firm*—Larson and Taylor

[57] ABSTRACT

An inspection device detects flooding in a hollow structural member such as the leg of an oil or gas rig so as to detect the presence of through wall cracks in the member. The device comprises an ultrasonic transducer for transmitting a pulsed beam of ultrasonic sound to pass through opposing faced walls or wall portions of the member and a visual indicator responsive to time spaced echoes of the ultrasonic beam reflected respectively from the opposing walls or wall portions and received by the transducer to indicate the presence or absence of flooding in the member. The transducer is located in the bridge plate of a jig and its beam passes through an aperture in a support frame of the jig. The support frame has a pair of spaced magnetic feet attached to a bracket on the frame and a further magnetic foot secured to the frame, the feet permitting the jig to be clamped onto a steel rig member so that the transducer can be optimally aligned with the member to optimize received echoes.

The bridge plate is movable in two orthogonal planes by adjusting control knobs so as to optimize alignment. A further visual indicator also responsive to the echoes from the transducer is adjustable to indicate whether the transducer is optimally aligned and only when the transducer is optimally aligned is the presence of flooding, if indicated by indicator, taken to be valid.

15 Claims, 6 Drawing Figures

DEVICE FOR DETECTING FLOODING OF A HOLLOW STRUCTURE

The present invention relates to an inspection device for detecting flooding of a hollow structure, particularly an underwater structure thereby to indicate through-going cracks in the structure.

The non-destructive detection of fatigue cracks in underwater structural members may be carried out by simple visual inspection and current practice tends to rely heavily on this method.

Experience during routine inspection of welds in underwater structures however has shown that tight surface-breaking fatigue cracks cannot readily be detected by the eye and thus it becomes necessary to use more sophisticated and reliable procedures such as the known magnetic crack detection method.

However even with this more advanced procedure cracks can only be reliably detected if the surface of the structural member is dressed, the magnetic field correctly aligned and sufficiently intense, and a high standard of illumination used with background paint.

Thus with undressed irregular welded profiles, a poor standard of lighting, difficult access and an unpleasant environment, even the conventional magnetic crack detection method has proved to be an unreliable means of detecting fatigue cracks in hollow structural members.

An object of the present invention is to provide an inspection device for detecting through walls cracks in structural members particularly underwater structural members, in a more reliable and efficient way than heretofore possible.

This is achieved by making use of the large difference which exists between the acoustic properties of water compared with air. Thus much greater attenuation occurs when ultrasound is transmitted through air than through water and much greater losses occur at a steel-/air boundary as compared with those at a steel/water boundary.

The presence or absence of water in a hollow structural member for example in the case of an underwater structural member, can therefore be readily detected by transmitting an ultrasonic pulse in towards the centre of the member and interpreting all resulting echoes due to reflection of the pulse by the walls of the structural member in the path of the pulse, and by inference whether a through-going crack is present in the member.

According to the invention therefore is provided an inspection device for detecting flooding of a hollow structural member comprising an ultrasonic transducer for emitting a pulsed beam of ultrasonic sound, means arranged to mount the transducer to the structural member at a spacing therebetween so that the beam path is directed to pass through opposing spaced walls or wall portions of the member, and indicating means responsive to time-spaced echoes of the ultrasonic pulsed beam reflected respectively from said opposing walls or wall portions and received by said transducer, to indicate the presence or absence of flooding in the member.

The advantage of such an inspection device is that it enables an entire structure to be inspected quickly without involved preparatory work, and at comparatively frequent intervals with a high probability of successfully detecting all serious through-going crack defects.

The means for mounting the transducer to the structural member preferably includes spaced magnetic feet which therefore allow the device to be magnetically clamped to the structural member when made of a suitable material.

Thus when using the device to test steel underwater structures an operator is free to secure his position with one hand while controlling the device with the other.

The device may advantageously be provided with an alignment means for aligning the ultrasonic beam with respect to the wall of the structural member to which the device is attached.

This enables a reflected echo signal with a favourable signal/noise ratio to be produced, the necessary alignment of the mean being monitored by interpreting the pulse form of the first echo received from that wall of the member.

The indicating means may be in the form of an electronic circuit for monitoring the echoes received from the structural member and providing representative signals which can then be displayed on an oscilloscope.

In this way the inspection device can be readily and easily controlled, and interpretation of the results produced by the device quickly analized.

Other features and advantages of the present invention will become apparent from the description of a preferred embodiment of the invention which follows.

Figure 2A:
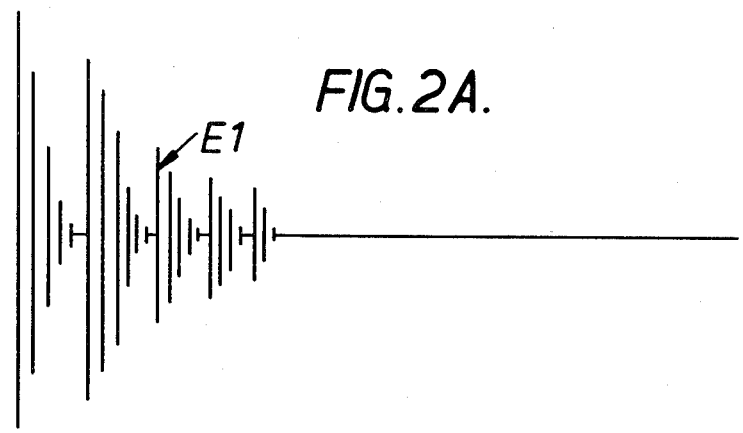
Figure 2B:
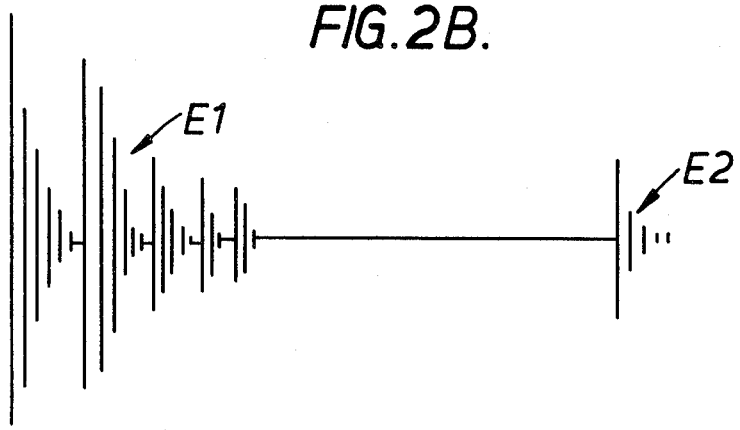
Figure 3:
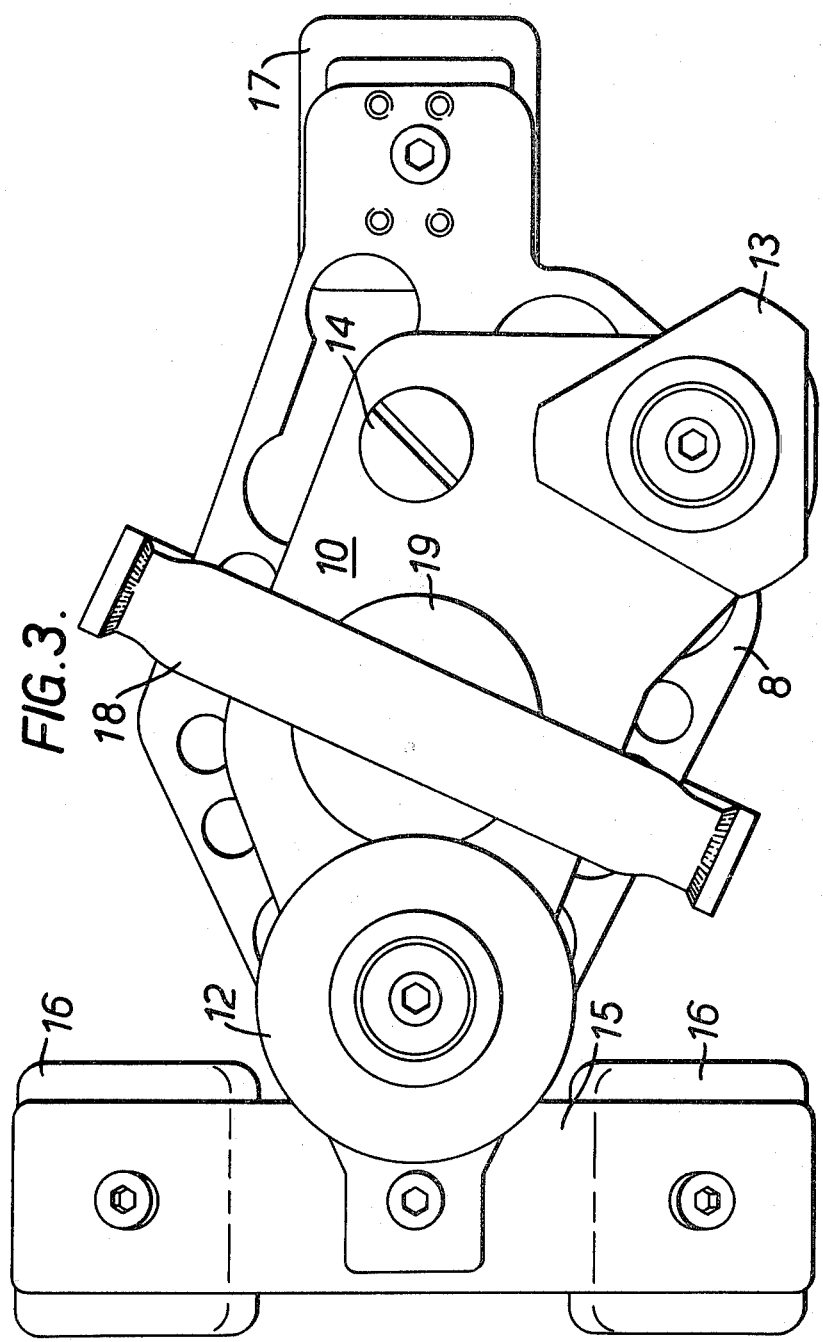
Figure 4:
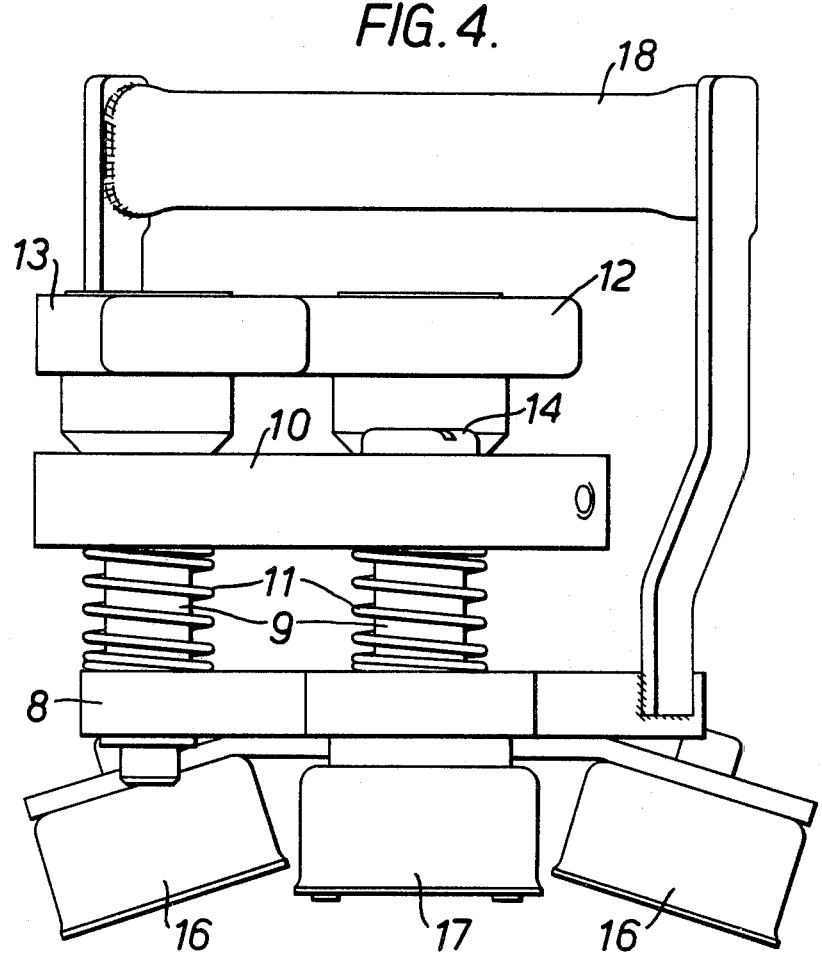
Figure 5:
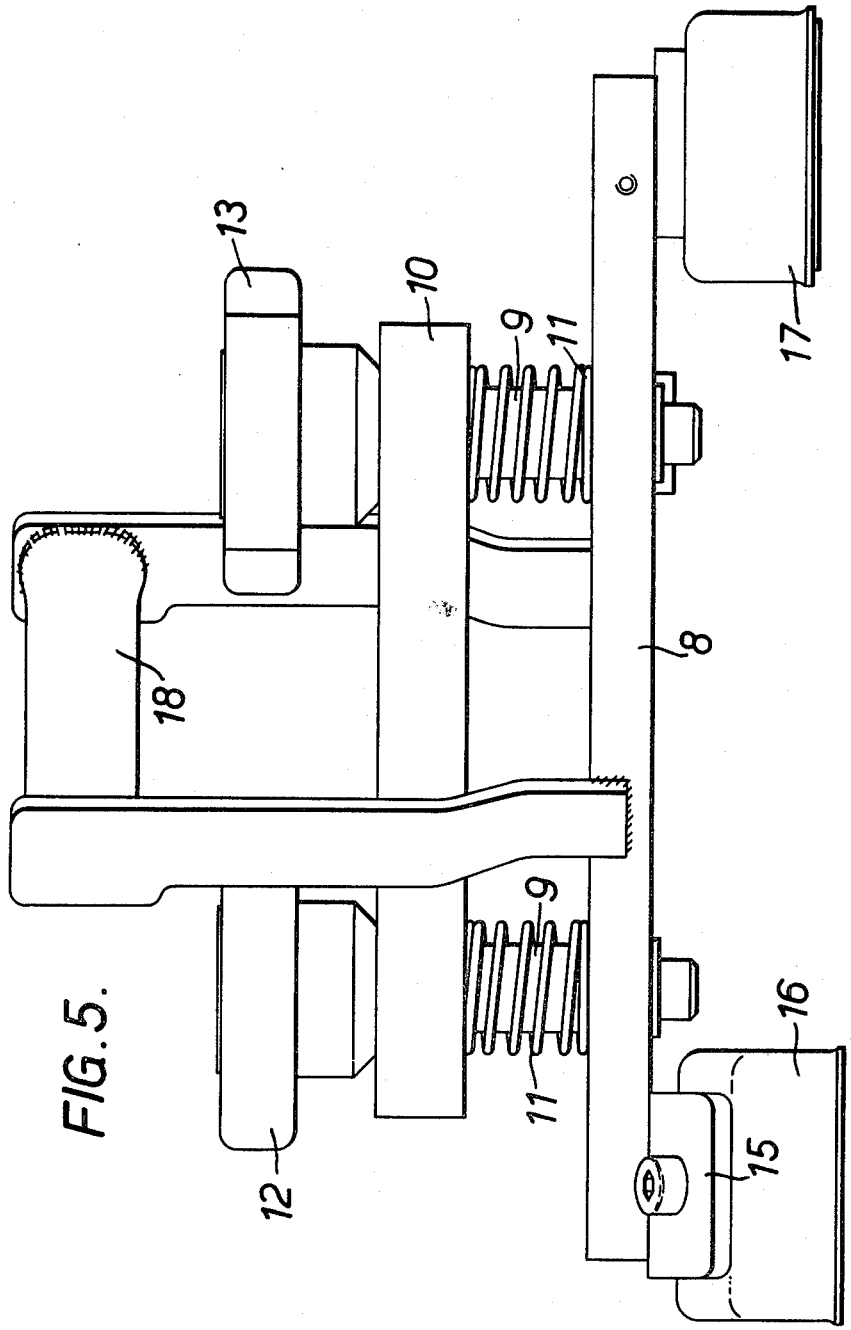
Figure 6:
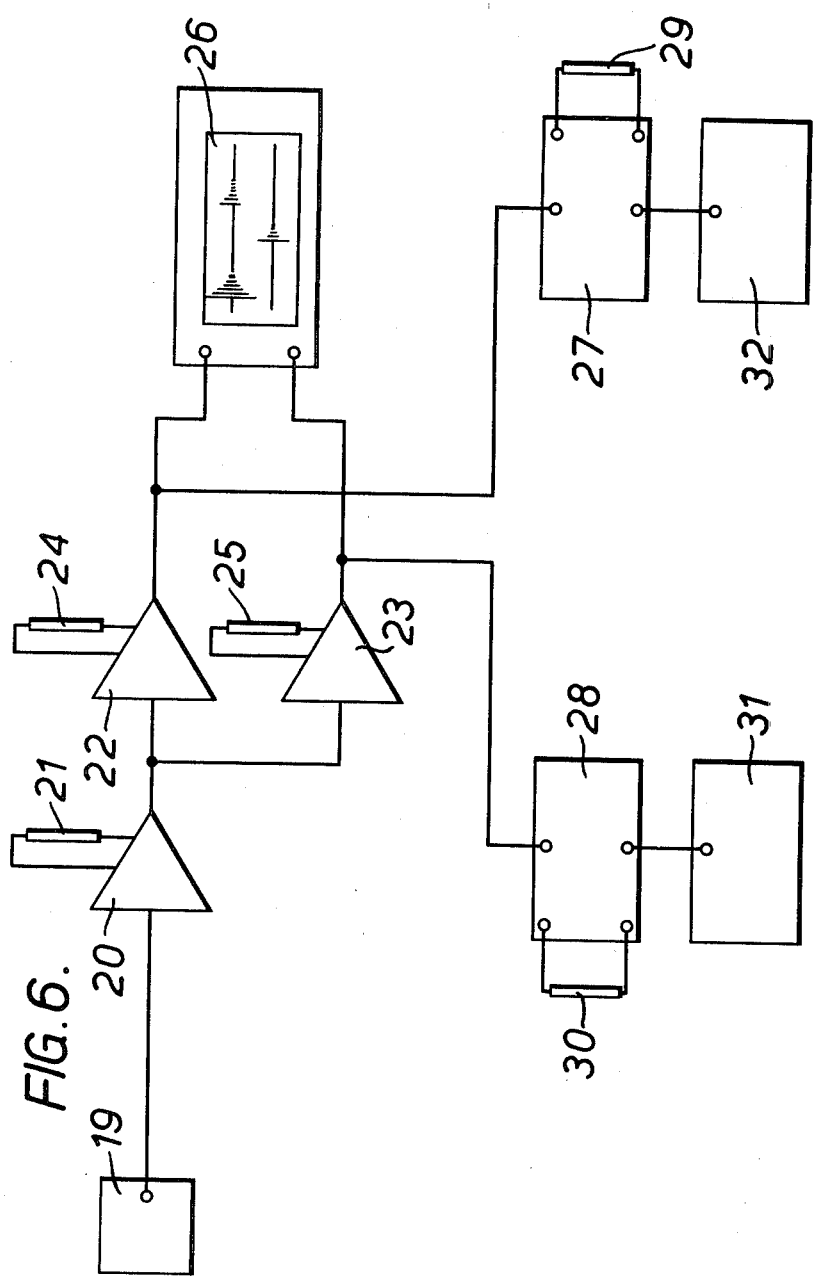

An embodiment of the present invention will now be described by way of example with reference to the accompanying drawings wherein:

FIG. 1 is an illustration of the concept of ultrasonic detection of flooding in a hollow structural member, FIG. 2A shows an oscilloscope trace of a first wall echo received from a structural member under test using the ultrasonic crack detection technique illustrated in FIG. 1 and indicative of a non-flooded condition of the structural member, FIG. 2B shows an oscilloscope trace of time-spaced echoes received respectively from opposing walls of a structural member under test using the ultrasonic crack detection technique illustrated in FIG. 1 and indicative of a flooded condition of the structural member, FIG. 3 is a plan view of an ultrasonic crack detection testing jig, FIG. 4 is a front view of the jig of FIG. 3, FIG. 5 is an end view of the jig of FIG. 3, and FIG. 6 is a schematic diagram of an electronic monitoring and transmitting circuit of an ultrasonic inspection device.

The concept underlying the present invention is illustrated in FIG. 1 which shows a hollow structural member 1 partially filled with water 2 up to a level 3.

A first ultrasonic transducer 4 for emitting short bursts of ultrasonic energy is positioned with respect to a wall face 5 of the member 1 such that the pulsed beam is normal thereto. In the illustration the structural member 1 is an underwater structure so that the signals for operating the transducer 4 are received through an umbilical S from a vessel or other rig (not shown) situated on the water surface.

The pulsed beam from the transducer 4 is directed into a non-flooded part of the member 1. Due to the poor transmission of ultrasound energy across the steel-/air interface the beam is reflected at the face 5 without transmission so that the transducer 4 only receives echoes reflected from that wall face.

A second similar ultrasonic transducer 6 is positioned such that its pulsed beam of ultrasound energy is directed to that part of the member which is flooded with water 2. In this case due to the good transmission across the steel/water interface two echoes are received by the transducer 6, the first one being a reflected echo from the wall face 5 and the other, with time delay, from the interior wall face 7 of an opposing wall of the structural member in the path of the pulsed ultrasound beam.

The resulting echoes E1 and E2 received by the transducers 4 and 6 are illustrated as oscilloscope traces in FIGS. 2A and 2B respectively.

It can be clearly seen that the presence of the second echo E2 as shown in FIG. 2B, may be taken to be an unambiguous indication that the member 1 is flooded.

The reliability of the technique is maximal when all echoes received are accounted for. This can be accomplished by knowing the velocity of sound propagation in water and steel and the dimensions of the structural member to be inspected, from which the arrival times of expected echoes can be calculated. Any echoes which cannot be accounted for indicate some ambiguity in the procedure.

A jig for carrying the ultrasonic transducer of the inspection device is shown in detail in FIGS. 3, 4 and 5.

The jig comprises a support frame 8 having three spaced screw mounted control shafts 9. A bridge plate 10 is mounted for movement on the shafts 9, the bridge plate 10 being continuously urged into spaced relationship from the support frame 8 by means of coiled springs 11 surrounding each shaft 9.

Two of the control shafts 9 are provided with actuable control knobs 12 and 13, the control knob 12 being of circular configuration and the control knob 13 of triangular configuration for identification purposes. The remaining control shaft 9 is provided with a setting screw 14. The control knobs 12 and 13 and the setting screw 14 bear against the upper surface of the bridge plate 10 so that the spatial relationship between the bridge plate 10 and the support frame 8 can be varied by actuation thereof.

The support frame 8 is provided on its underside with a bracket 15 having a magnetic foot 16 attached to each free end of the bracket 15. The free ends of the bracket 15 are angled obtusely to the central portion so that the feet 16 can be readily clamped partially around a tubular structural member under test.

A further magnetic foot 17 is attached to the support frame 8, the positional relationship between the two magnetic feet 16 and the magnetic foot 17 being such that the mounting positions of the feet lie at the corners of an isoceles triangle and the mounting position of the foot 17 being at the apex of the isosceles triangle.

As an alternative to the arrangement described the feet 16, 17 could be arranged on the support frame 8 each to lie in a flat plane thereby to enable the jig to be clamped to a flat surface. Clearly the feet 16, 17 could also be adjustably mounted in some suitable way so that the jig could be clamped to surfaces of varying shapes.

The support frame 8 is provided with a handle 18 to enable an operator to manipulate the device into a test position.

An ultrasonic transducer 19 is mounted to the bridge plate 10, the support frame 8 being provided with an aperture (not shown) to permit passage of ultrasound to and from the transducer 19. Since the transducer is mounted to the bridge 10 it will be appreciated that its spacing from the structural member under test can be varied by actuation of control knobs 12 and 13 and setting screw 14. Furthermore the shafts 9 carrying the control knobs 12 and 13 are so arranged on the frame 8 that individual actuation of knobs 12 and 13 enables the bridge plate 10 to be moved in two orthogonal planes so that the ultrasound beam can be properly aligned with respect to the structural member under test thereby to optimise received echoes.

The ultrasonic transducer 19 mounted to the jig as shown in FIGS. 3, 4 and 5, is capable of generating short bursts of ultrasound energy in the frequency range 0.1 and 5 MHz and may be adapted for underwater use if required.

The transducer 19 is coupled to an electronic circuit as shown in FIG. 6, for monitoring received signals of reflected ultrasound from the transducer 19.

The circuit comprises a preamplifier 20 provided with a gain control 21 for amplifying the received signals of reflected ultrasound from the transducer 19.

The amplified signals are first fed to the inputs of a high gain amplifier 22 and a low gain amplifier 23 each respectively provided with gain controls 24 and 25. The amplifiers 22 and 23 are coupled to an oscilloscope 26 having two separate time base axes.

The low gain amplifier 23 is used to monitor the first received reflected wall echo from a structural member under test and therefore requires less gain than the amplifier 22 used for monitoring the later time-spaced echo received from an opposing wall of the structural member under test and in the path of the ultrasonic pulsed beam.

The outputs of the amplifiers 22 and 23 are also monitored by gated demodulators 27 and 28 respectively, the gates of these demodulators being indicated by reference numerals 29 and 30 respectively.

Gate 30 of demodulator 28 is set on the lower trace of the oscilloscope 26 so that if the transducer 19 is properly aligned with respect to the immediately adjacent wall of a structural member under test, the resulting reflected echo falls between the delay limits or gate interval and amplitude limit imposed by the gate 30. The gate 30 is adjusted initially according to the known external dimensions of the structural member under test and the distance of the transducer from the wall of the structural member to which it is clamped.

A visual alignment indicator 31 is coupled to the demodulator 30 and is thus activated by the gate 30 to display a green light when optimum alignment of the ultrasonic beam has been achieved.

On the other hand gate 29 of demodulator 27 is set on the upper trace of the oscilloscope 26 so as to activate a visual indicator 32 coupled thereto only if the later time-spaced echo falls within a delay limit and amplitude limit imposed by the gate 29 thus giving a visual indication of flooded conditions. This limit is again dependent on the external dimensions of the member under test and the separation of the ultrasonic transucer from the front wall of the structural member to which it is clamped. Upon activation the flooded member indicator 32 displays a red light but with the arrangement shown the indicator 32 is invalid until the alignment indicator 31 shows green.

With the system as described it is possible to determine the wall thickness of a member under test by measuring the time interval between signal echoes displayed on the oscilloscope screen 26. Wall thickness measurements however can only be made when the member is fully cleaned underneath the ultrasonic transducer and the appropriate frequency transucer is used.

The electronics for the ultrasonic inspection device as described may be positioned separately from the transducer jig. For example during underwater inspection the transducer jig is connected to the electronics via an umbilical cable, the electronics being carried on board a ship or rig on the water surface. In this case a diver operating the jig would have to rely on instructions from a distant source thus limiting somewhat the versatility of the device. Thus it would be quite feasible to incorporate the electronics in the transducer jig itself so that the diver can make the appropriate adjustments to optimise alignment of the transducer beam and to thereafter determine whether or not the member under test is flooded without reference to a remote controlling source.

We claim:

1. An inspection device for detecting flooding of a hollow structural member, comprising an ultrasonic transducer for emitting a pulsed beam of ultrasonic sound, means for mounting said transducer to the structural member at a spacing therebetween so that the beam path is directed to pass through opposing spaced walls or wall portions of the member, and indicating means responsive to time-spaced echoes of the ultrasonic pulsed beam reflected respectively from said opposing walls or wall portions and received by said transducer to indicate the presence or absence of flooding in the member, said mounting means comprising alignment means for aligning the beam with the structural member thereby to optimise the amplitude of the first received one of said echoes.

2. A device as claimed in claim 1 wherein said mounting means comprises a support frame.

3. A device as claimed in claim 2 wherein said mounting means further comprises one or more magnetic feet attached to said support frame for magnetically clamping the support frame to the member.

4. A device as claimed in claim 3, wherein said mounting means comprises three magnetic feet arranged in spaced relationship on said frame, said magnetic feet being mounted at the respective ends of a bracket attached to the frame and shaped to permit the device to be clamped to a tubular structural member with said feet attached to said bracket spaced around the tubular member.

5. A device as claimed in claim 2, wherein said support means comprises a bridge plate and wherein said alignment comprises means for resiliently urging said bridge plate away from said support frame and means for adjusting the spacial relationship beteen the bridge plate and said frame and thus the distance between the transducer and a structural member under test.

6. A device as claimed in claim 19, wherein said means for adjusting the spacial relationship between the bridge plate and said frame comprises at least three shafts screw mounted to said frame, said bridge plate being movably mounted on said shafts, and control means for actuating the shafts thereby to adjust the position of said bridge plate with respect to said frame.

7. A device as claimed in claim 6, wherein each of said shafts is provided with a coiled spring mounted around each shaft between said bridge plate and said frame to resiliently urge said bridge plate away from said frame.

8. A device as claimed in claim 6 wherein said control means comprises a setting screw for one shaft and a circular-shaped actuating knob and a triangular-shaped actuating knob for the other two shafts respectively.

9. A device as claimed in claim 8, wherein said shafts carrying said actuating knobs are arranged on the frame such that individual actuation thereof moves said bridge plate in two orthogonal planes thereby to enable optimal alignment of the transducer beam with respect to a structural member under test.

10. A device as claimed in claim 1 wherein said indicating means comprises electronic circuit means for monitoring said echoes and providing signals representative thereof, and an oscilloscope responsive to said signals for visual display of said time-spaced reflected echoes.

11. A device as claimed in claim 10 wherein said electronic circuit means includes a first visual indicator for indicating reception of a first echo displayed on a lower trace of said oscilloscope from the nearest one of said opposing walls or wall portions corresponding to correct alignment of the beam with respect thereto, and a second visual indicator for indicating reception of a second echo displayed on an upper trace of said oscilloscope from the farthest one of said opposing walls or wall portions subsequent to activation of said first visual indicator and indicative of flooding of the member.

12. A device as claimed in claim 11, wherein said first visual indicator is coupled to a first gated demodulator, the gate of which is set on the lower trace of said oscilloscope thereby to effect activation of said first visual indicator when said first echo falls between a time delay and amplitude limit imposed by said gate of said first demodulator.

13. A device as claimed in claim 11 wherein said second visual indicator is coupled to a second gated demodulator the gate of which is set on the upper trace of said oscilloscope thereby to effect activation of said second visual indicator when said second echo falls within a delay limit and amplitude limit imposed by the gate of said second demodulator.

14. A device as claimed in claim 12 wherein said limit imposed by the gate of said first demodulator is dependent on the distance of path of travel of the ultrasonic beam between said opposing walls or wall portions of the structural member and the separation of the ultrasonic transducer from the wall of the structural member to which it is mounted.

15. A device as claimed in claim 13 wherein said limit imposed by the gate of said second demodulator is dependent on the distance of path of travel of the ultrasonic beam between said opposing walls or wall portions of the structural member and the separation of the ultrasonic transducer from the wall of the structural member to which it is mounted.

* * * * *